(12) United States Patent
Lee et al.

(10) Patent No.: US 7,087,775 B2
(45) Date of Patent: Aug. 8, 2006

(54) METHOD FOR PREPARATION OF ORGANIC CHELATE

(75) Inventors: Ke Ho Lee, San 26-4, Samsan-ri, Nangseong-myeon, Cheongwon-gun, Chungcheongbuk-do 363-861 (KR); Sang-Bum Lee, San 24, Samsan-ri, Nangseong-myeon, Cheongwon-gun, Chungcheongbuk-do 363-861 (KR)

(73) Assignees: Koko Enterprise Co., Ltd., Seoul (KR); Ke Ho Lee, Chungcheongbuk-do (KR); Sang-Bum Lee, Chungcheongbuk-do (KR)

( * ) Notice: Subject to any disclaimer, the term of this patent is extended or adjusted under 35 U.S.C. 154(b) by 0 days.

(21) Appl. No.: 11/115,553

(22) Filed: Apr. 26, 2005

(65) Prior Publication Data

US 2005/0283013 A1 Dec. 22, 2005

(30) Foreign Application Priority Data

Jun. 22, 2004 (KR) .................. 10-2004-0046707

(51) Int. Cl.
*C07F 1/08* (2006.01)
*C07F 3/06* (2006.01)
*C07F 13/00* (2006.01)
*C07F 15/02* (2006.01)
*C07F 15/06* (2006.01)

(52) U.S. Cl. ................... 556/50; 556/116; 556/134; 556/148

(58) Field of Classification Search ............... 556/50, 556/116, 134, 148
See application file for complete search history.

(56) References Cited

U.S. PATENT DOCUMENTS

| | | | | |
|---|---|---|---|---|
| 3,950,372 | A | * | 4/1976 | Abdel-Monem ............. 556/50 |
| 4,172,072 | A | * | 10/1979 | Ashmead ................... 530/345 |
| 4,181,672 | A | * | 1/1980 | Popper et al. ............... 556/50 |
| 4,764,633 | A | * | 8/1988 | Anderson et al. ............ 556/50 |
| 4,830,716 | A | * | 5/1989 | Ashmead ................... 205/457 |
| 5,278,329 | A | * | 1/1994 | Anderson ................... 556/50 |
| 5,430,164 | A | * | 7/1995 | Abdel-Monem et al. ....... 556/2 |
| 5,698,724 | A | * | 12/1997 | Anderson et al. ............ 556/50 |
| 6,407,138 | B1 | * | 6/2002 | Ashmead et al. ........... 514/492 |
| 6,426,424 | B1 | * | 7/2002 | Ashmead et al. ............. 556/1 |
| 6,458,981 | B1 | * | 10/2002 | Ashmead et al. ............ 556/50 |
| 6,670,494 | B1 | * | 12/2003 | Trusovs ..................... 556/49 |
| 6,710,079 | B1 | * | 3/2004 | Ashmead et al. ........... 514/492 |
| 6,992,203 | B1 | * | 1/2006 | Trusovs ..................... 556/50 |
| 2004/0097748 | A1 | * | 5/2004 | Abdel-Monem et al. ...... 556/48 |

* cited by examiner

*Primary Examiner*—Porfirio Nazario-Gonzalez
(74) *Attorney, Agent, or Firm*—Bachman & LaPointe, P.C.

(57) ABSTRACT

A method for the preparation of organic chelates utilized as ingredients of animal feedstuffs. The organic chelates are passed to the intestines of livestock without decomposition in the stomach, and thereby have a high absorption rate. The present invention provides a preparation method of perfect chelate minerals having a high yield and containing copper, zinc, iron, manganese, or cobalt. The organic chelate mineral is prepared by precipitating metal sulfates or chlorides with sodium hydroxide or potassium hydroxide in a solution of two equivalents of an amino acid completely dissolved at above 70° C., collecting metal hydroxide by removing sodium sulfate, potassium sulfate, sodium chloride or potassium chloride through filtering, dissolving the metal hydroxide by adding the equivalent weights of hydrochloric acid, and then neutralizing the hydrochloric acid added for dissolving metal hydroxide.

5 Claims, 3 Drawing Sheets

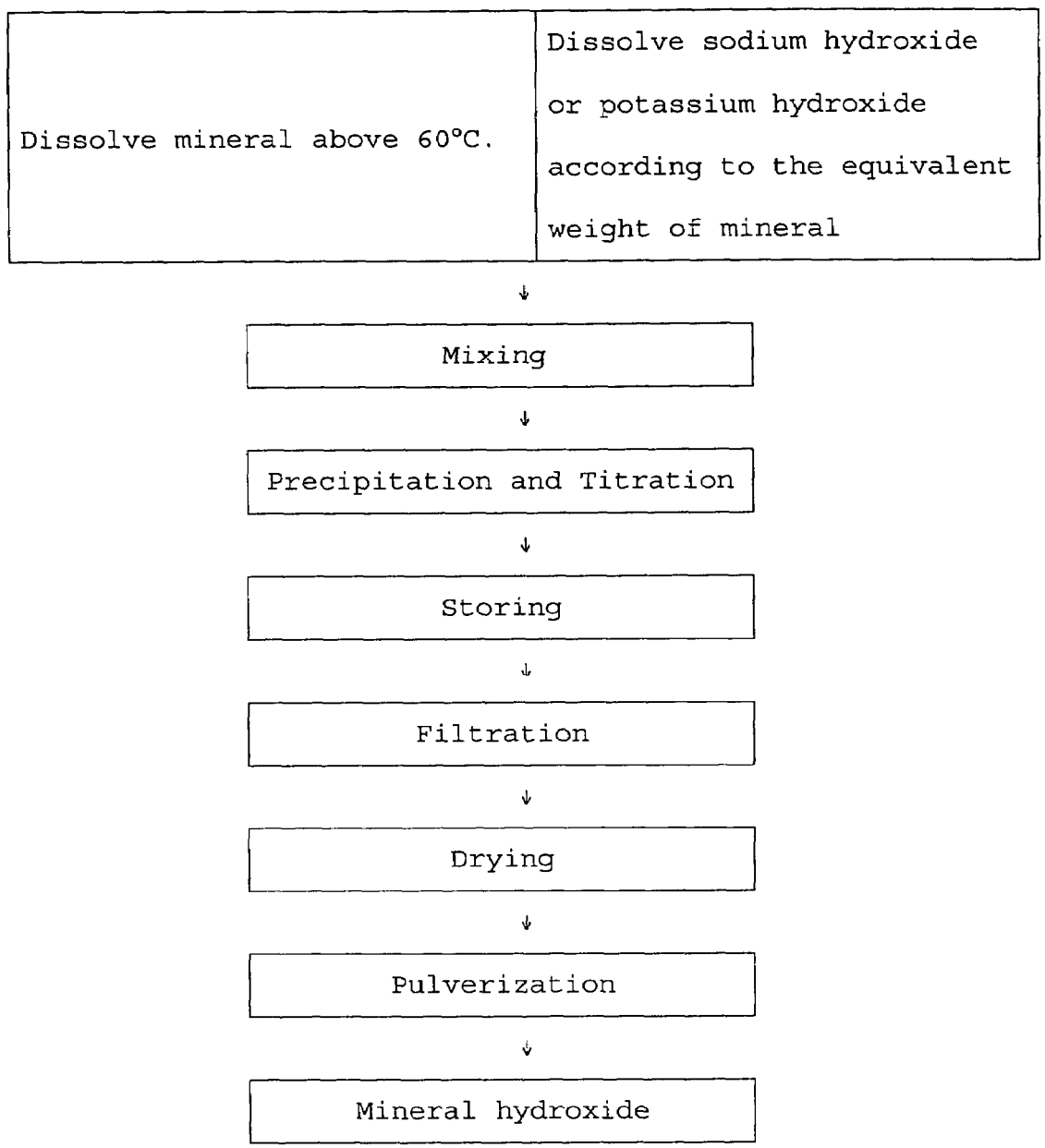
<Fig. 1a>

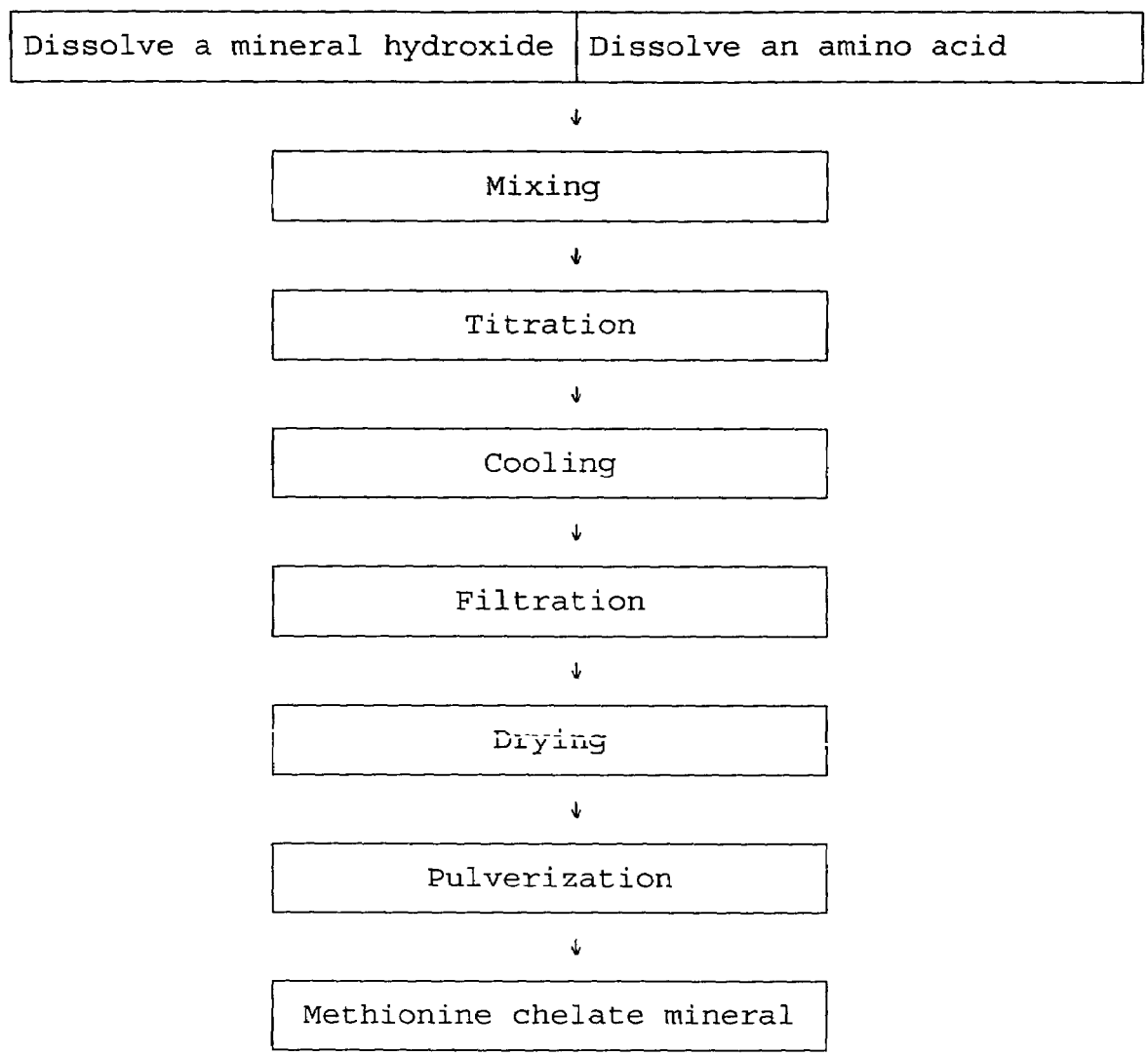
<Fig 1b>

<Fig. 2>
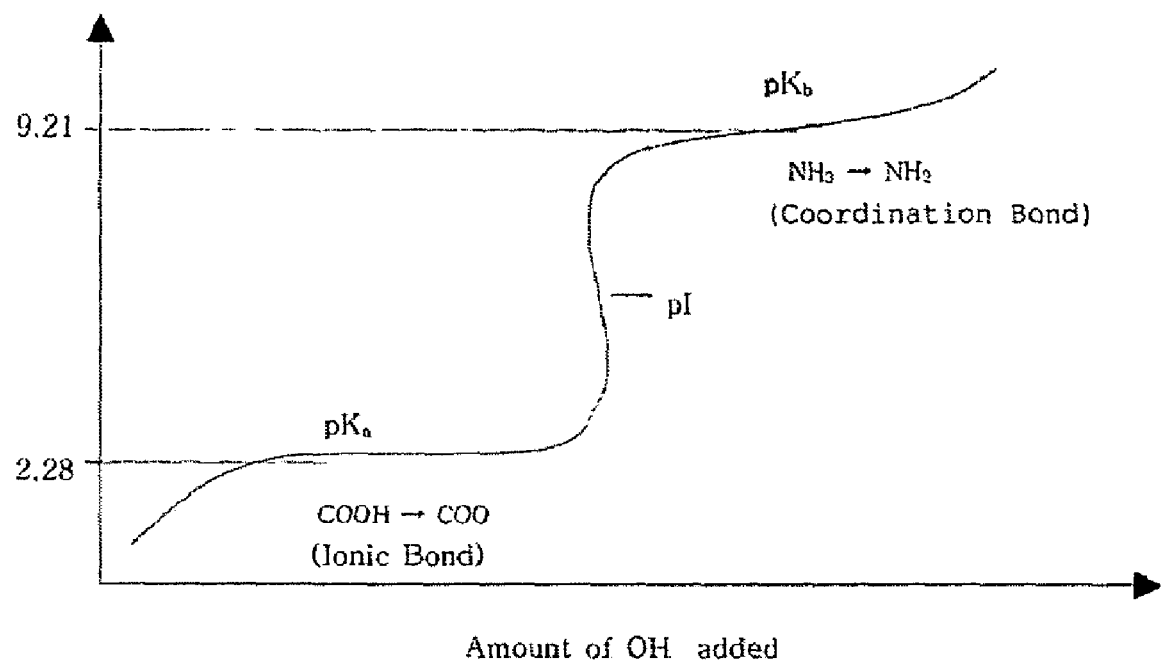

METHOD FOR PREPARATION OF ORGANIC CHELATE

BACKGROUND OF THE INVENTION

1. Field of the Invention

The present invention relates to a method for the preparation of organic chelates and, more particularly, to a method for the preparation of organic chelate minerals with a high absorption rate having the organic chelates used as ingredients for animal feedstuffs that are not easily decomposed in a stomach and delivered to the intestines.

2. Description of the Related Art

Properly assorted animal feedstuffs containing various kinds of nutrients have been developed and used to improve productivity of livestock which is a major source of proteins for humans. Specific amounts of iron, copper, zinc, and potassium are essential for the normal growth of the livestock. Even though the contents of minerals are very low in an animal, they have various functions such as forming skeleton, adjusting an osmotic pressure within a body, maintaining an acid-base balance of the body fluids, and acting as an activator in an enzymatic system or a constituent of enzyme itself. These minerals are supplied to the livestock from external sources since they are not synthesized in the body. Therefore, these minerals should be contained in the animal feedstuff to feed the livestock. Inorganic minerals according to the prior art have the salt forms of chlorides, sulfates, nitrates, phosphates, and carbonates. However, the absorption rate of inorganic minerals in a living body is so low that excessive amounts of minerals are fed to the livestock. Unabsorbed minerals are excreted as feces, which are then recycled to the soil. Through this process, the accumulated minerals, which give fatal damages to the ecosystem of the soil, increase the soil contamination.

An introduction of organic chelates has been suggested to solve the problems cited hereinbefore since organic chelates may highly be absorbed in a living body. Because of a high absorption rate of organic chelates in a living body, a relatively small amount of organic chelates included in the animal feedstuff fulfills the metabolic requirement of minerals and reduces the soil contamination. In the late 1980's, it was reported that organic chelates prepared from the reaction of metal compounds and carbohydrates or proteins have a high absorption rate of 70~80% in comparison with that of the inorganic minerals (Kratzerand Vohr. 1986).

The term of chelate is not a new concept. It is adopted from the structure of a divalent iron or a magnesium ion located respectively in the center of hemoglobin or chlorophyll and surrounded by organic amino acids or porphyrins. The chelates, hemoglobin and chlorophyll are essential compounds in maintaining the life of living things.

For examples, Korean Patent Publication (hereinafter referred to KP) number 1991-5777, 2000-53858, 2002-6112, 2002-6113, and 2002-6114 are disclosed to provide organic minerals. KP No. 1991-5777 relates to a method for preparation and utilization of easily absorbable iron proteinate into the body and discloses a method for the preparation of iron proteinate by chelating divalent iron ion with oligopeptide obtained from the hydrolysis of proteins. KP Nos. 2002-6112, 2002-6113 and 2002-6114 relate respectively to a method for the preparation of easily absorbable copper proteinate into the body, a method for the preparation of sodium proteinate that is not ionized in the vein after absorption in the body, and a method for the preparation of easily absorbable zinc proteinate into the body. These inventions disclose the methods for preparation of chelate compounds having metal ion oligopeptide by the following procedure. Oligopeptides are produced by adding 2~4 weight % protease and reacting the proteins suspended in purified water at pH 3.5 to 6.0 for 11 to 12 hrs. A chelate reaction between a mineral ion such as copper, sodium, or zinc and the above oligopeptides is occurred so that a metal ion oligopeptide chelate is formed. The above prior arts have disadvantages that the procedures are complicated and require high preparation cost since minerals are bonded to the proteolytic products. KP No. 2000-53858 relates to a preparation method of metal chelates and utilization in animal feedstuff, and discloses a preparation method of organic chelates as follows. Metal oxide, metal powder, metal carbonate, or metal hydroxide is added to amino acid or the hydrolyzed product of animal/vegetable proteins in water at the pH 5.5–8.5, and then the mixture is heated up in the range from 60° C. to boiling point of the solution in inert atmosphere. However, metal powder, metal oxide, metal carbonate, and metal hydroxide are sparingly soluble in water, and the above metal ions are not completely ionized in the solution. The disclosed inventions have a disadvantage that in the above pH range, only ionic bond is formed and coordination bond is not formed, so that the chelate formation between metal ion and amino acid is not accomplished. This method does not show any specific effect compared to the method using inorganic minerals in animal feedstuff.

Additionally, KP 2003-6877 relates to a manufacturing method of animal feedstuff additives containing methionine-iron chelates. According to this method, the ratio of methionine and iron is 1:1 or 1:2 and the dissolving temperature of methionine should be below 70° C. The methionine, however, is not completely soluble in the suggested temperature and the above method describes simply that an alkali solution is utilized. If a high reactive material such as potassium or sodium hydroxide is used in the alkali solution and the reaction of $FeSO_4 + NaOH \rightarrow Fe(OH)_2 + Na_2SO_4$ progresses completely, then a chelate compound may be formed. However, the solubility of methionine is dramatically increased due to the formation of the salt form, $-COO^-M^+$, between $-COO-$ of methionine and $M^+$ (sodium or potassium) of alkali, and thereby the dissociation between methionine and metal ion is caused. Accordingly, the bonding between methionine and divalent iron ions may partially be formed, however inorganic salts such as iron hydroxide and iron sulfate may also be formed at the same time.

A chelate mineral as a single amino acid mineral chelate having a high absorption rate and buffering capability is not yet disclosed up to now internationally. Chelate products according to the prior art do not have a concrete coordination bonds and features as a single amino acid chelate. In this regard, the organic chelates having a high absorption rate are not yet developed so far. Commercially available single amino acid chelates are produced by an evaporation, condensation and drying processes, indicating that concrete bonding is not yet induced.

SUMMARY OF THE INVENTION

An object of the present invention is to provide organic chelates having perfect ionic and coordination bonds between an amino acid and a metal ion.

To achieve this object, the present invention provides a preparation method of organic chelate having the following chemical formula 1. The present invention comprises the steps of: (1) dissolving in water an amino acid and a salt containing mineral to form coordination bonds and precipitating hydroxide salt by sodium or potassium hydroxide; (2) removing water soluble salts such as potassium sulfates, sodium sulfates, potassium chlorides, or sodium chlorides by a filter press; (3) dissolving the filtered hydroxide mineral of M(OH)$_2$ (where, M is a metal ion) in hydrochloric acid; (4) mixing amino acid by completely dissolving in the above solution; (5) titrating the amino acid solution slowly with sodium hydroxide upto the pI value of methionine solution; and (6) filtering and drying the particles formed by the titration.

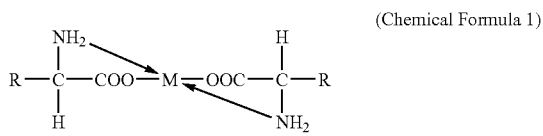

(Chemical Formula 1)

wherein M is a divalent metal ion such as copper, iron, zinc, manganese, and cobalt, and R is a side chain of amino acid.

In the above preparation method, the step (4) of mixing an amino acid is carried out by mixing two equivalents of completely dissolved amino acid with one equivalent of a metal in the solution containing salt free metal hydroxide dissolved in hydrochloric acid. Metal sulfate or metal chloride is used to prepare metal hydroxide. The metal hydroxide is precipitated in the reaction between metal salt and sodium hydroxide or potassium hydroxide. It is necessary to remove residual salt, as possible, such as sodium sulfate, potassium sulfate, sodium chloride, or potassium chloride, because perfect chelate formation is hindered due to the formation of ionic bonding between residual sodium or potassium ions and amino acids.

In the above preparation method, the step (5) of titration is carried out by adding sodium hydroxide or potassium hydroxide of equivalent weight to the hydrochloric acid added to help dissolving metal hydroxide.

The amino acids used in the present invention are not limited to specific amino acids, however methionine is preferably utilized.

Although the prior art somewhat induces chelating bond in terms of chemical equation, perfect chelation is not formed according to the properties of mineral, because the supply of only OH$^-$ ion is not possible in the titration step to the increase of pH for the bonding between a mineral and an amino acid and also excessive sodium or potassium ions from sodium or potassium hydroxide combines with COO$^-$ ion of amino acid. This is a problem in the prior art.

However, according to the present invention, the aqueous solution of salt containing mineral for the formation of coordination with an amino acid is added to sodium or potassium hydroxide so that salt free metal hydroxide is obtained. The metal hydroxide dissolved in hydrochloric acid contains abundant OH$^-$ ions, which remove H$^+$ from —NH$^{3+}$ in amino acid and induce perfect coordination bond between a metal ion and an amino acid.

BRIEF DESCRIPTION OF DRAWINGS

FIG. 1 is a schematic flow chart describing preferable process according to the present invention.

FIG. 2 is a titration curve of methionine in the preparation process of methionine-manganese chelate according to an example embodiment of the present invention.

DETAILED DESCRIPTION OF THE PREFFERED EMBODIMENTS

Hereinafter, a preparation method of an organic chelate in accordance with the present invention will be described in more detail with reference to the accompanying drawings.

FIG. 1a shows a pretreatment process of a mineral before the preparation of organic chelates according to the present invention. FIG. 1b shows a process flow chart regarding the preparation of an organic chelate from metal hydroxide and an amino acid. The object of the pretreatment process shown in FIG. 1a is to form a perfect coordination bond by eliminating excessive sodium and potassium ions. 2(OH$^-$) ions produced in the process are used for the removal of the proton in —NH$_3^+$ group bonded in the alpha carbon of amino acid. Without the above pretreatment process, the reaction in the solution may not lead to a perfect formation of salts such as potassium sulfate or potassium chloride, and alternatively sodium sulfate or sodium chloride. Therefore, this is the most important process.

Exemplary, non-limiting embodiments of the present invention will now be described more fully hereinafter. This invention may, however, be embodied in many different forms and should not be construed as limited to the exemplary embodiments set forth herein.

EXAMPLE 1

Preparation Method of Manganese, Iron, Cobalt, Copper, and Zinc-Methionine Chelates In preparing zinc-methionine, the mixing ratio is determined by estimating an amino acid to manganese (II) ion ratio of 2:1 since manganese ion is divalent. According to the mixing ratio of 2:1, the amount of manganese sulfate monohydrate is 53.15 g corresponding to 93.8 g of methionine. The manganese sulfate monohydrate is put into a 2 liter beaker and completely dissolved with 1 liter water at 50~60° C. 25.7 g of 98% sodium hydroxide flake is put into another beaker and dissolved slowly with about 50 ml water at room temperature. The sodium hydroxide solution is slowly added to the manganese sulfate solution. Subsequently, water at about 60° C. is added to the mixed solution so that the total volume becomes 1800 ml, and the mixed solution is strongly stirred by an overhead stirrer. The viscosity of the solution is increased and then decreased at the end of the reaction. When the viscosity is lowered, stirring is stopped and the solution is left for a specific time to precipitate salts. The supernatant is carefully removed and the precipitate is filtered by vacuum filter for the maximum elimination of a solution containing sodium sulfate as possible. Maximum bonding may be induced by stronger filtration (Highly purified metal hydroxide may be obtained by a salt removal process in the industry).

The precipitate of manganese hydroxide on the filter paper (Whatman cat. No. 1441.185) is carefully removed from the funnel of filtering device and placed on a 2 liter beaker, and the manganese hydroxide is carefully separated from the filter paper. As the filtration is performed sufficiently, the precipitate becomes harder, and thereby separation of precipitate becomes easier. The manganese hydroxide obtained by the above procedure is put into a 2 liter beaker, about 900 ml of warm water at above 60° C. is added, and then 62 g (50 ml) of concentrated hydrochloric acid is slowly added while stirring. After stirring for a few minutes, a solution having abundant manganese chrolide is obtained. This solution is then mixed with a solution containing 93.8 g of methionine completely dissolved in 800 ml of hot water at about 90° C., wherein higher temperature is preferable for the mixed solution.

An equivalent of hydrochloric acid (about 62 g of concentrated HCl) added to help dissolution of manganese hydroxide is the same as the equivalent of sodium hydroxide (24 g of 98% NaOH). The mixed solution is slowly titrated with the 24 g of sodium hydroxide dissolved in high concentration. Theoretically the above sodium hydroxide solution may be completely consumed at pH 5.74, which is the pI value of methionine. However, there may be a slight difference of pH value due to the deviations both in the preparation process of manganese hydroxide and in the addition of hydrochloric acid. Since pH of the pI value is in the equivalent point, the pH changes very sensitively. The perfect chelate bond may be obtained by observing the pH changes per quantity of the added sodium hydroxide solution (1 ml ΔpH) during a precise titration.

In other words, when each 1 ml of concentrated aqueous solution of sodium hydroxide is added in every titration, the end point corresponds to the point where a sudden pH change is observed. This is to neutralize only the hydrochloric acid added for dissolving the metal hydroxides.

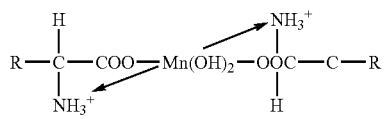

In the above chemical formula, if the ionic bonding between manganese and carboxylic group (COO—) is formed in the ratio of 2:1, extra amount of 2(OH)⁻ removes H⁺ of amino group, and then isolated electron pair is formed to give real chelation. However, manganese hydroxide is not soluble in a solution, and hydrochloric acid is thereby used to disassociate the manganese hydroxide. Using the principle that a strong acid reacts completely with a strong base, only the amount of sodium hydroxide required to neutralize the hydrochloric acid is added by drop to induce the bonding more effectively. After the titration, the beaker is submerged partially in a large water vessel containing cold water, which is placed under the overhead stirrer, and the solution is cooled down with stirring. If the reaction mixture is filtered by using a vacuum filter after the temperature of the solution reached near the room temperature, the manganese-methionine chelate mineral is obtained on the filter paper at a surprisingly high speed.

A cobalt, zinc, iron, or copper-methionine chelate may be prepared according to the above procedure. The yield of bond formation is much higher, compared to the case that methionine mixed with solution of mineral sulfate or chloride is titrated with sodium hydroxide or potassium hydroxide solution. According to the conventional method of simple titration of mixture, the yield of the product varies according to the kind of mineral, because pH range of precipitation varies according to the kind of a mineral. In the present invention, although the quantities of sodium hydroxide and potassium hydroxide used for precipitation look different, the amount of sodium hydroxide required to precipitate is affected only by the differences of both water temperature and equivalent point corresponding to a molecular weight in the precipitation process.

EXAMPLE 2

Preparation Method of Iron-Methionine Chelate Mineral

With a similar method to the above procedure, iron hydroxide obtained by precipitating 87.4 g of iron sulfate heptahydrate is dissolved by adding hydrochloric acid and mixed with 93.8 g of methionine with stirring, and then titrated with sodium hydroxide to neutralize additional hydrochloric acid. Subsequently, iron-methionine chelate mineral is prepared by a cooling, filtering, and drying process.

EXAMPLE 3

Prepararation Method of Cobalt-Methionine Chelate Mineral

With a similar method to the above procedure, cobalt hydroxide obtained by precipitating 74.8 g of cobalt chloride hexahydrate with addition of 22.9 g of sodium hydroxide is dissolved by adding 50 ml (62 g) concentrated hydrochloric acid and mixed with 93.8 g of methionine with stirring, and then titrated with sodium hydroxide (24 g). Subsequently, cobalt-methionine chelate mineral is obtained by a cooling, filtering, and drying process.

EXAMPLE 4

Preparation Method of Zinc-Methionine Chelate Mineral

With a similar method to the above procedure, zinc-methionine chelate mineral is obtained by using 93.8 g of methionine and zinc hydroxide precipitated from 90.4 g of zinc sulfate heptahydrate.

EXAMPLE 5

Preparation Method of Copper-Methionine Chelate Mineral

With a similar method to the above procedure, copper-methionine chelate mineral is obtained by using 93.8 g of methionine and copper hydroxide precipitated from 78.5 g of copper sulfate pentahydrate.

Table 1 is provided for the reference.

TABLE 1

| Mineral | Molecular weight | pH without precipitation | Remarks |
|---|---|---|---|
| $ZnSO_4 \cdot 7H_2O$ | 287.56 | 8.0 | 2:1 Equivalent weight of mineral for methionine 93.8 g:90.4064 g, used NaOH:19.25 g |
| $CuSO_4 \cdot 5H_2O$ | 249.69 | 6.5 | 2:1 Equivalent weight of mineral for methionine 93.8 g:78.5 g, used NaOH:18.3 g |
| $CuCl_2 \cdot 2H_2O$ | 170.48 | 6.5 | 2:1 Equivalent weight of mineral for methionine 93.8 g:53.6 g, used NaOH:18.33 g |
| $MnSO_4 \cdot H_2O$ | 169.08 | 11.0 | 2:1 Equivalent weight of mineral for methionine 93.8 g:56.16 g, used NaOH:25.7 g |
| $MnSO_4 \cdot 5H_2O$ | 241.08 | 11.0 | 2:1 Equivalent weight of mineral for methionine 93.8 g:75.79 g, used NaOH:25.7 g |
| $MnCl_2 \cdot 4H_2O$ | 197.9 | 11.0 | 2:1 Equivalent weight of mineral for methionine |

TABLE 1-continued

| Mineral | Molecular weight | pH without precipitation | Remarks |
|---|---|---|---|
| gSO$_4$ | 120.37 | 11.5 | 93.8 g:62.21 g, used NaOH:25.7 g 2:1 Equivalent weight of mineral for methionine |
| MgSO$_4$.7H$_2$O | 246.48 | 12.0 | 93.8 g:37.84 g, used NaOH:24.75 g 2:1 Equivalent weight of mineral for methionine |
| FeSO$_4$.7H$_2$O | 278.02 | 8.0 | 93.8 g:77.49 g, used NaOH:26.12 g 2:1 Equivalent weight of mineral for methionine |
| CoCl$_2$.6H$_2$O | 237.93 | 10.0 | 93.8 g:87.40 g, used NaOH:25.21 g 2:1 Equivalent weight of mineral for methionine 93.8 g:74.8 g, used NaOH:22.92 g |

Various kinds of amino acid chelates may be easily prepared by calculating weight of minerals corresponding to the amount of methionine or another amino acid, dissolving, titrating, and converting the amount of hydroxide titrated to reach an equivalent point.

The above pH is measured at room temperature, and an experiment may more easily be carried out by estimating the amount of sodium hydroxide required for the same volume of the solution and at the same temperature.

The preparation of chelate mineral is completed when titration reaches a neutral point. More than 80% of sodium chloride produced as a by-product, methionine reacted with Na or K, and unreacted methionine may be removed in the filtering process. A highly pure manganese-methionine chelate mineral is produced according to this procedure.

Although it may be assumed that considerable amount of material passes through the filter paper, the loss is actually in very low level with regard to the yield of the product. A manganese-methionine chelate mineral may not be obtained by titrating mixture of the above two solutions with sodium hydroxide or potassium hydroxide. If the pH of the mixture is raised to 11.5, methionine is bonded to an excessive amount of sodium ion. Therefore, sodium salt of methionine passes through the filter paper and only manganese hydroxide remains on the filter paper. It will be clearly seen that filtration yield is very low in a filtering process.

In the above salt removal process, if the bonding and bonding ratio are not obtained perfectly, the components not involved in the bond formation will be removed. Therefore, the reaction should be performed securely step by step. The removed sodium sulfate or sodium hydroxide may be recycled by ion-separation membrane electrolysis, and high efficiency in a mass production may be obtainable, if hydroxide minerals, such as manganese hydroxide, are prepared in a dried powder form by filter press in advance.

The organic chelate in accordance with the present invention has buffering capability, because a coordination bond with metal is formed by the change (—NH$_3^+$→—NH$_2$+H$^+$), as shown in the following chemical formula 2. The organic chelate in accordance with the present invention has higher possibility that the mineral is easily absorbed in a living body of animal or human without dissociation in the stomach by gastric acid, as compared to conventional products. Especially, if the chelate mineral mixed in animal feedstuff is dissociated by gastric acid, the proteins in animal feedstuff are hydrolyzed to peptons by the protease pepsin produced from the precursor pepsinogen activated by stimulation of gastric acid. If organic mineral products are dissociated at that time, the separated metal ions pass through a stomach and are neutralized by basic bile, and the ionic formation is occurred between metal ions and a lot of peptones around them so that macromolecule is formed because the number of peptones is greater than that of methionine. Thus the assertion that the metal ions may be easily absorbed due to the low molecular weight is not acceptable.

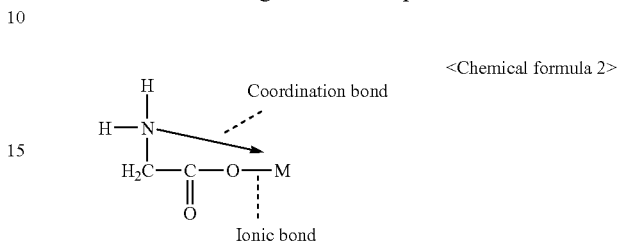

<Chemical formula 2>

Although chelate minerals of 1:1 bond structure are produced from 2:1 bond structure due to the dissociation by the attack of hydrochloric acid, and pass through the stomach, it is evident that the 1:1 bond structure combines with high molecular weight compounds through neutralization reaction by bile. In other words, only when 2:1 bond structure is formed perfectly, high absorption rate of mineral is maintained, because the possibility of recombination with macromolecule is still low, even though the coordination bond (Met—Mn+HCl(H$^+$Cl$^-$)) is cleaved and then reacts with two protons from hydrochloric acid, which leads a first buffer state (chemical formula 3).

<Chemical Formula 3>

$$R-\underset{\underset{H}{|}}{\overset{\overset{NH_3^+}{|}}{C}}-COO-M-OOC-\underset{\underset{NH_3^+}{|}}{\overset{\overset{H}{|}}{C}}-R \quad + \quad 2Cl^-$$

A preparation method of an organic chelate in accordance with the present invention provides a chelate product having perfect coordination bonds between lone electron pair of an amino acid and a mineral. When the organic chelate prepared in accordance with the present invention is taken by animal or human, the possibility of dissociation by the gastric acid is far lower than that of conventional products, and absorption efficiency of a dosed chelate mineral is increased. Therefore, a less amount of dosing is required and the excreted quantity of a mineral is significantly decreased. The organic chelate in accordance with the present invention further has an effect of decreasing soil contamination.

Although the invention has been described in detail herein, it should be understood that the invention is not limited to the embodiments herein disclosed. Various changes, substitutions and modifications may be made thereto by those skilled in the art without departing from the spirit or scope of the invention as described and defined by the appended claims.

What is claimed is:

1. A preparation method of an organic chelate having the structure of following chemical formula 1 comprising the steps of:
   1) precipitating metal hydroxides by using sodium hydroxide or potassium hydroxide after dissolving a salt containing mineral to be coordination-bonded with an amino acid in the water;
2) removing water soluble salts such as potassium sulfate, sodium sulfate, potassium chloride or sodium chloride from a aqueous solution by filter press;
3) dissolving the filtered metal hydroxides $M(OH)_2$ (wherein M is a metal ion) in hydrochloric acid;
4) dissolving an amino acid completely and mixing in the solution;
5) titrating slowly with sodium hydroxide until reaching the pI value of an amino acid;
6) filtering and drying produced particles;

<Chemical Formula 1>

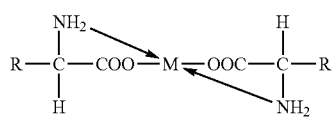

wherein M is copper, iron, zinc, manganese, or cobalt, and R is a side chain of an amino acid.

2. The preparation method of an organic chelate of claim 1, wherein in the step (4) two equivalents of the amino acid completely dissolved, one equivalent of the metal hydroxide, and the hydrochloric acid for dissociation are mixed.

3. The preparation method of an organic chelate of claim 1, wherein the metal hydroxide is prepared by precipitating a mineral of a metal sulfate or metal chloride.

4. The preparation method of an organic chelate of claim 1, wherein in the step (5) perfect ionic and coordination bond are formed by titrating with aqueous solution of the sodium hydroxide equivalent to the added hydrochloric acid.

5. The preparation method of an organic chelate of claim 1, wherein the amino acid is a methionine.

* * * * *